(12) United States Patent
Szweda et al.

(10) Patent No.: US 8,936,582 B2
(45) Date of Patent: Jan. 20, 2015

(54) IMPLANTABLE MEDICAL PORT WITH ALIGNMENT FEATURE

(75) Inventors: Gina M. Szweda, Cincinnati, OH (US); Stephen M. Torain, Cincinnati, OH (US); Scott A. Woodruff, Boston, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 237 days.

(21) Appl. No.: 13/215,270

(22) Filed: Aug. 23, 2011

(65) Prior Publication Data
US 2013/0053783 A1 Feb. 28, 2013

(51) Int. Cl.
| | | |
|---|---|---|
| A61M 37/00 | (2006.01) |
| A61M 31/00 | (2006.01) |
| A61M 39/10 | (2006.01) |
| A61M 39/02 | (2006.01) |
| A61M 39/12 | (2006.01) |

(52) U.S. Cl.
CPC ....... *A61M 39/1011* (2013.01); *A61M 39/0208* (2013.01); *A61M 39/12* (2013.01); *A61M 2039/0223* (2013.01); *A61M 2039/1044* (2013.01)
USPC ...................... 604/288.02; 600/37

(58) Field of Classification Search
CPC ............. A61M 39/1011; A61M 39/0208; A61M 39/12; A61M 2039/1044; A61M 2039/0023
USPC ............. 285/242; 600/37; 604/175, 533; 606/151
See application file for complete search history.

(56) References Cited

U.S. PATENT DOCUMENTS

| | | | |
|---|---|---|---|
| 4,673,394 A | 6/1987 | Fenton, Jr. et al. | |
| 5,178,612 A * | 1/1993 | Fenton, Jr. ................. | 604/533 |
| 5,312,337 A | 5/1994 | Flaherty et al. | |
| 6,067,991 A | 5/2000 | Forsell | |
| 6,461,292 B1 | 10/2002 | Forsell | |
| 6,470,892 B1 | 10/2002 | Forsell | |
| 7,351,240 B2 | 4/2008 | Hassler, Jr. et al. | |
| 7,390,294 B2 | 6/2008 | Hassler, Jr. et al. | |
| 7,416,528 B2 | 8/2008 | Crawford et al. | |
| 7,442,165 B2 | 10/2008 | Forsell | |
| 7,621,863 B2 | 11/2009 | Forsell | |
| 7,699,770 B2 | 4/2010 | Hassler, Jr. et al. | |
| 7,775,215 B2 | 8/2010 | Hassler, Jr. et al. | |
| 7,850,660 B2 | 12/2010 | Uth et al. | |
| 8,016,745 B2 | 9/2011 | Hassler, Jr. et al. | |

OTHER PUBLICATIONS

U.S. Appl. No. 12/917,544, filed Nov. 2, 2010, Vendely.
Australian Office Action, Examiner's First Report, dated Aug. 16, 2013 for Application No. AU 2012211394.

\* cited by examiner

*Primary Examiner* — Jacqueline Cheng
*Assistant Examiner* — Kaylee Wilson
(74) *Attorney, Agent, or Firm* — Frost Brown Todd LLC

(57) ABSTRACT

An apparatus comprises a port, a catheter, a sleeve in communication with the catheter, and an alignment feature. The port is configured to be in fluid communication with an implantable band. The port comprises a septum operable to be pierced by a needle. The catheter is configured to establish fluid communication between the port and the implantable band. The catheter is further configured to deliver fluid to the implantable band. The sleeve is configured to interface with the port. The alignment feature is responsive to the catheter being fully secured to the port. The alignment feature prevents the port from being fully sutured to tissue unless the catheter is fully secured to the port.

1 Claim, 7 Drawing Sheets

IMPLANTABLE MEDICAL PORT WITH ALIGNMENT FEATURE

BACKGROUND

Implantable medical devices may be implanted in a patient to perform a therapeutic function for that patient. Non-limiting examples of such devices include pace makers, access ports (such as vascular access ports, infusion ports, and ports used with gastric band systems, etc.) and gastric pacing devices. Such implants may need to be attached, perhaps subcutaneously, in an appropriate place in order to function properly. It may be desirable that the procedure to implant such devices be quick, easy and efficient.

Ports may be placed beneath the skin of a body for injecting fluids into or withdrawing fluids from the body. By way of example, vascular access ports may be used for infusing medication, blood draws, and many other applications. Injection ports may be used for adding or withdrawing fluid in adjustable gastric band systems. These various access ports may include an implantable port housing coupled to a fluid conduit which delivers fluid to or withdraws fluid from a location in the patient's body (e.g., a vein or a gastric band, etc.).

Gastric band systems are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly in order to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of implantable access ports and gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various embodiments of ports having tissue in-growth promoting surfaces and/or features are depicted and described as being part of a gastric band system, the tissue in-growth surfaces and features may be employed with other types of implantable medical ports or other medical devices. Accordingly, the drawings and descriptions should be regarded as illustrative in nature and not restrictive.

I. Exemplary Gastric Band System

FIGS. 1-4 illustrate an exemplary gastric band system (10). As shown, gastric band system (10) comprises an injection port (12), a gastric band (20), and a flexible conduit (or catheter) (18). Injection port (12) of the present example comprises a port housing (14), a needle penetrable septum (16) and a fluid reservoir (not shown in FIGS. 1-4) located beneath septum (16). A needle may pierce septum (16) to reach the reservoir and add or withdraw fluid (e.g., saline, etc.). Catheter (18) (e.g., a flexible and/or resilient polymeric tube) is attached to port housing (14) and is in fluid communication with the fluid reservoir therein. In particular, catheter (18) is slid over a barbed stem (not shown in FIGS. 1-4), which extends from port housing (14) and is in fluid communication with the fluid reservoir beneath septum (16). After catheter (18) is slid over the barbed stem, a retention sleeve (19) is slid over catheter (18) in the region near port housing (14), to squeeze catheter (18) against the barbed stem, such that retention sleeve (19) assists in keeping catheter (18) secured to the barbed stem.

Figure 1:
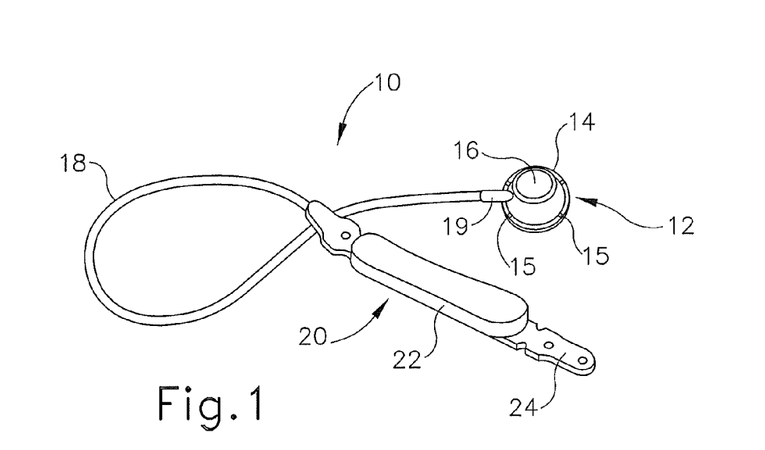
FIG. 1 depicts a perspective view of an implantable portion of an exemplary gastric band system, including an injection port having an integral fluid conduit retention sleeve.

Port housing (14) may comprise a unitary structure (e.g., a one piece housing insert molded about septum (16), etc.). Alternatively, port housing (14) may be assembled from two or more mating components such as a port body that at least partially receives a port base therein. Port housing (14) may be formed of titanium, plastic, or any other suitable material or combination of materials. Septum (16) may be formed of silicone or any other suitable material or combination of materials.

Injection port (12) may be subcutaneously secured over a patient's sternum, to the patient's abdominal fascia, or in any other suitable location. By way of example, port (12) may be sutured in place using the suture apertures (15) located about the periphery of port housing (14). In some other versions, injection port (12) may be configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. For example, injection port (12) may be configured to include a plurality of fasteners that are selectively deployed from the injection port in order to secure the port in place within a patient, as further described in U.S. Pub. No. 2005/0283118, issued as U.S. Pat. No. 7,850,660. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Catheter (18) may be formed of silicone or any other suitable material or combination of materials. In the present example, catheter (18), bladder (22), and injection port (12) form a closed fluid circuit. Accordingly, a needle that is inserted through septum (16) into the underlying reservoir may be used to add fluid to or withdraw fluid from inflatable bladder (22) in order to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
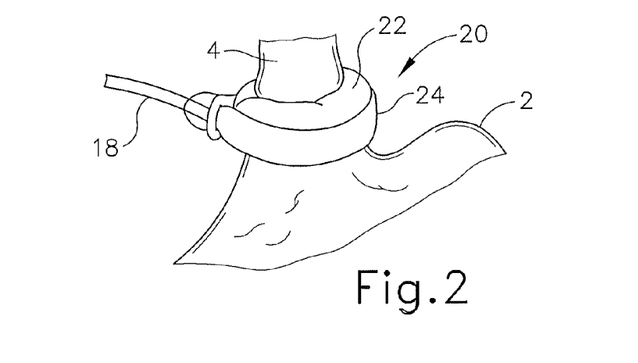
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
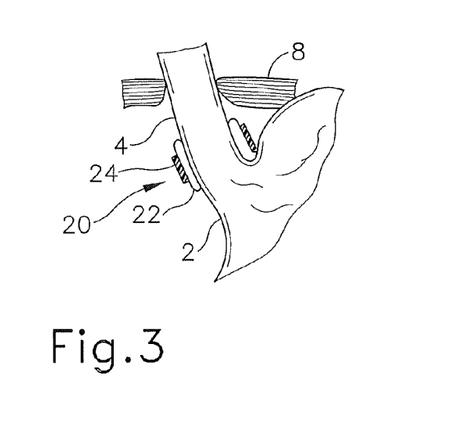
FIG. 3 depicts a cross-sectional view of the gastric band of FIG. 1, showing the band positioned around the gastro-esophageal junction of a patient in a deflated configuration.
Figure 4:
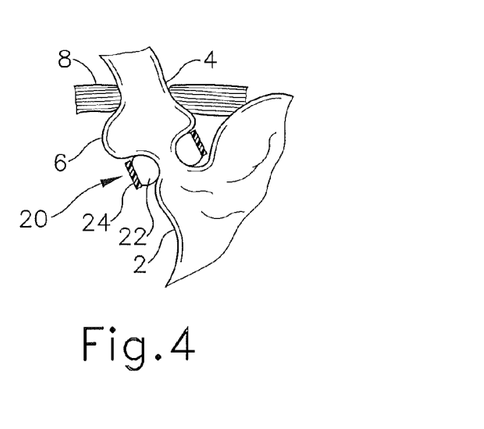
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

It may be desirable to have a way of determining whether catheter (18) is properly coupled with the barbed stem of injection port (12). For example, in some instances, if catheter (18) is not properly secured over the barbed stem, catheter (18) may leak as fluid is being delivered from injection port (12) to gastric band (20). In examples described herein, suture apertures (15) are used to suture injection port (12) into place within the patient. Thus, it may be desirable to prevent injection port (12) from being fully sutured in place until catheter (18) and the barbed stem are in fact sufficiently secured together. Various examples will be described below that relate to structures for preventing injection port (12) from being fully sutured in place until catheter (18) and the barbed stem are in fact sufficiently secured together. Other examples will be apparent to those of ordinary skill in the art in view of the teachings herein.

II. Exemplary Locking Connector with Suture Holes

Figure 5:
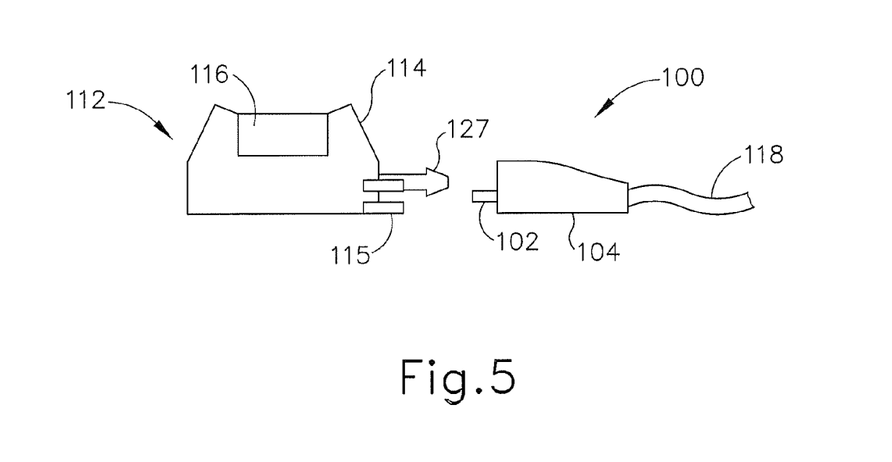
FIG. 5 depicts a side view of an injection port with an exemplary locking connector.

FIG. 5 shows an exemplary locking connector (100) for use with catheter (118). Locking connector (100) comprises a sleeve body (104) and an engagement feature (102). Sleeve body (104) serves as a retention sleeve, similar to retention sleeve (19) discussed above, to assist in securing catheter (118) to barbed stem (127) of injection port (112). Septum (116) is held within housing (114) of injection port (112) and may be pierced with a needle to inject fluid through catheter (118) when locking connector (100) and catheter (118) are coupled with barbed stem (127) of injection port (112).

Figure 6:
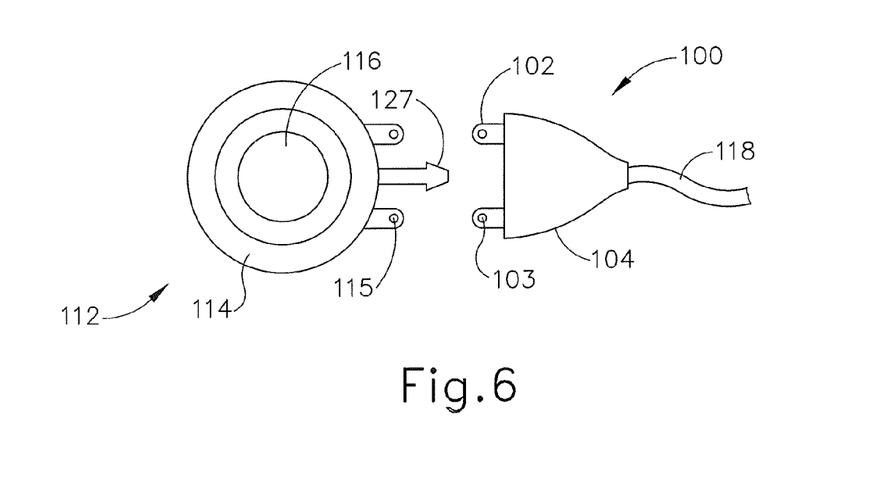
FIG. 6 depicts a top view of the exemplary injection port shown in FIG. 5.

Injection port (112) also defines suture apertures (115) through which sutures may be used to secure injection port (112) within a patient. As shown in FIG. 6, engagement feature (102) defines complementary apertures (103), which are shaped and positioned to complement suture apertures (115). As a result, once locking connector (100) is fully pressed against injection port (112), apertures (103) align with apertures (115) such that suture(s) may be guided through suture apertures (103, 115) into tissue. However, when apertures (103, 115) are not fully aligned (e.g., if locking connector (100) is only partially pressed against injection port (112), etc.), suture(s) would not have a clear path to pass through apertures (115), which would be blocked by engagement feature (102). While the present example shows a pair of suture apertures (115) and complementary apertures (103), it will be appreciated that any suitable number of suture apertures (115) and complementary apertures (103) may be used as would be apparent to one of ordinary skill in the art in view of the teachings herein. It is also contemplated that the number of suture apertures (115) need not necessarily equal the number of complementary apertures (103). For example, suture apertures (115) may outnumber complementary apertures (103).

In an exemplary use, a user may grasp locking connector (100) and press locking connector (100) against injection port (112) to establish a fluid tight connection between catheter (118) and injection port (112) by coupling catheter (118) and barbed stem (127). Once suture apertures (115) and complementary apertures (103) are aligned, the user may use that alignment as verification that locking connector (100) is properly connected with injection port (112) and that it is appropriate to pass sutures through suture apertures (115) to secure injection port (112) to the patient's tissue.

In some other exemplary versions, before complementary apertures (103) align with suture apertures (115), a hinged member or other suitable member may block suture apertures (115) until locking connector (100) is fully engaged with injection port (112). Once fully engaged, the hinged member is rotated by locking connector (100) thereby moving aside to reveal suture apertures (115). As yet another merely illustrative variation, catheter (118) may directly engage the hinged member to thereby move the hinged member to reveal suture apertures (115).

III. Exemplary Safety Trigger for Suture Holes

Figure 7:
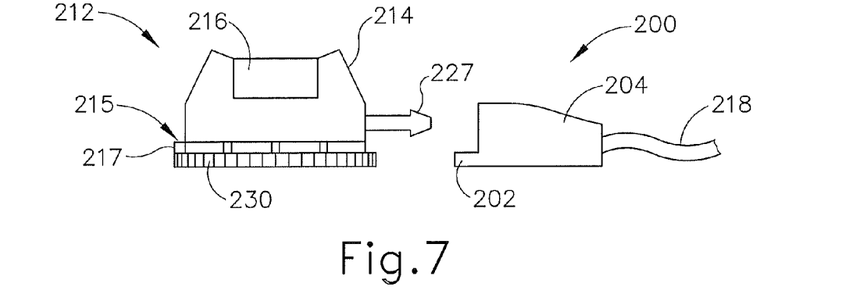
FIG. 7 depicts a side view of another exemplary version of an injection port with a locking connector and cover.
Figure 8:
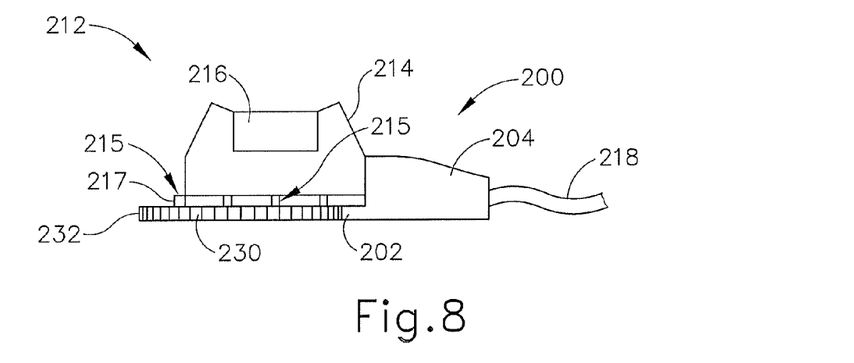
FIG. 8 depicts a side view of the injection port shown in FIG. 7 with the locking connector engaging the injection port.
Figure 9:
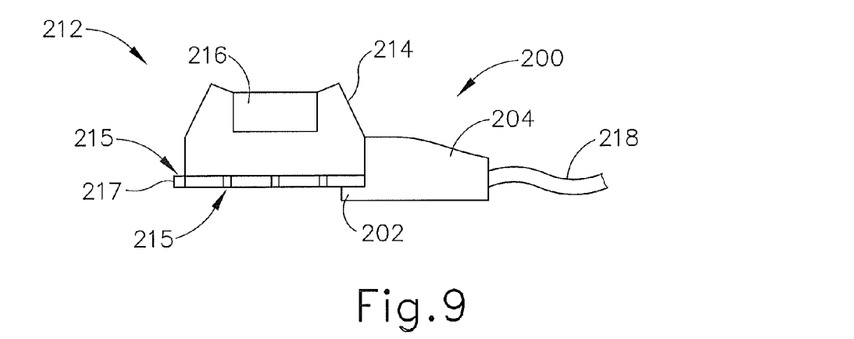
FIG. 9 depicts a side view of the injection port shown in FIG. 7 with the locking connector engaging the injection port and the cover removed.

In some exemplary versions, as shown in FIGS. 7-9, a cover (230) may be used to verify that it is suitable to pass sutures through suture apertures (115). In particular, FIG. 7 shows injection port (212) comprising a housing (214) with a septum (216) contained therein. A barbed stem (227) extends from housing (214) and provides fluid communication with a reservoir (not shown) that is defined by housing (214) beneath septum (216). Injection port (212) also comprises suture apertures (215) and a cover (230) slidably mounted to the bottom of injection port (212). In the present example, suture apertures (215) are formed through an annular flange (217) that extends outwardly from the bottom of housing (214). As shown in FIG. 7, cover (230) is configured to block the bottoms of suture apertures (215) when cover (230) is fully engaged with housing (214), such that cover (230) prevents sutures from fully passing through flange (217) via suture apertures (215). Locking connector (200) comprises a sleeve body (204) that engages injection port (212) to secure catheter (218) to barbed stem (227), thereby establishing fluid communication between injection port (212) and catheter (218).

Locking connector (200) further comprises engagement feature (202) operable to engage cover (230). In particular, engagement feature (202) is configured and positioned to push cover (230) along the bottom of housing (214) as locking connector (200) is pressed against injection port (212). FIG. 8 shows locking connector (200) engaging injection port (212) with engagement feature (202) pushing cover (230) out of its original position. In this distal, pushed position, cover (230) reveals a removal tab (232). The user may grasp removal tab (232) to simply remove cover (230) by pulling on removal tab (232) (e.g., using a conventional tissue grasping instrument, etc.). FIG. 9 shows injection port (212) after cover (230) has been removed. With cover (230) removed, suture apertures (215) are no longer blocked, allowing a user to pass suture(s) through suture apertures (215) to thereby secure injection port (212) to tissue in the patient.

IV. Exemplary Injection Port with Locking Members

Figure 10:
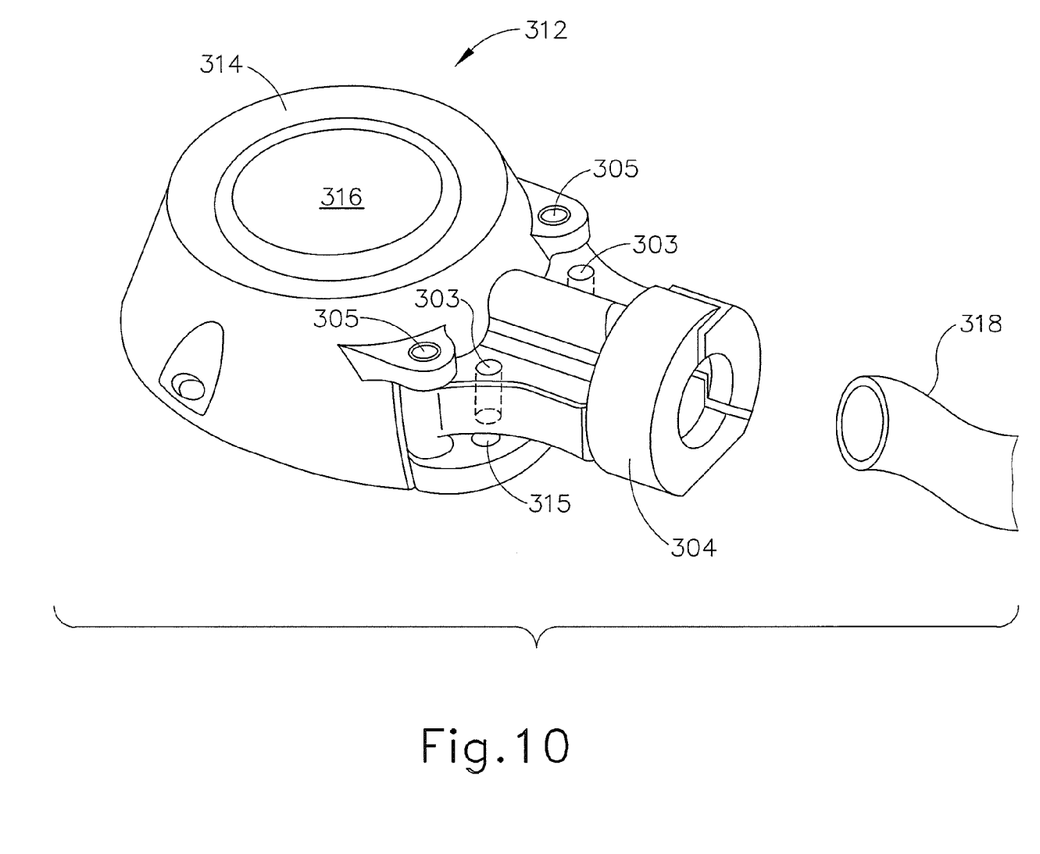
FIG. 10 depicts a top perspective view of an exemplary injection port with locking members in an fully closed position.
Figure 11:
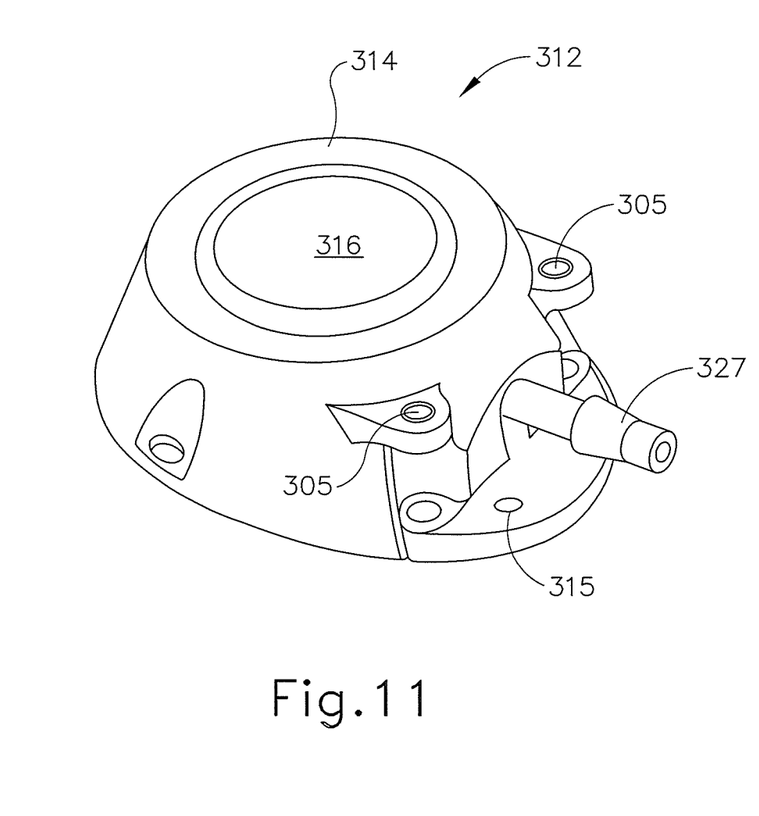
FIG. 11 depicts a top perspective view of the injection port shown in FIG. 10 with the locking members removed to show a barbed stem.

FIGS. 10-11 show an exemplary injection port (312) having a housing (314) with a septum (316) contained therein and a pair of suture apertures (315) that are formed through housing (314). A barbed stem (327) extends from housing (314) and is in fluid communication with a reservoir beneath septum (316). Injection port (312) further comprises a pair of half locking members (304) that are pivotally coupled with injection port (312) via respective pins (305). Locking members (304) are moveable between and open position to a closed position as shown in FIG. 10. When catheter (318) is slid over barbed stem (327), locking members (304) may be pivoted to the closed position to cooperatingly clamp catheter (318) against barbed stem (327), thereby helping to secure catheter (318) to barbed stem (327). Thus, catheter (318) may be connected to injection port (312) followed by closing locking members (304) upon catheter (318). While the exemplary version shows locking members (304) having a pair of jaws, other suitable versions may be used as would be apparent to one of ordinary skill in the art. For example, locking members (304) may comprise more than two pivoting jaws or a single member operable to lock catheter (318) into injection port (312). By way of example only, locking members (304) may be constructed in accordance with at least some of the teachings of U.S. patent application Ser. No. 12/917,544, entitled "Implantable Medical Port with Fluid Conduit Retention Sleeve," filed on Nov. 2, 2010, and issued Jul. 9, 2013 as U.S. Pat. No. 8,480,560, the disclosure of which is incorporated by reference herein.

Locking members (304) further define a pair of complementary apertures (303) that complement suture apertures (315) formed in housing (314) of injection port (312). Complementary apertures (303) and suture apertures (315) are positioned such that complementary apertures (303) and suture apertures (315) are only aligned when locking members (304) are in the fully closed position as shown in FIG. 10. When complementary apertures (303) and suture apertures (315) are aligned, then sutures and/or guide needles may be passed through apertures (303, 315) to secure injection port (312) to tissue in a patient. If locking members (304) are not fully closed, apertures (303, 315) will not align and sutures will not be able to pass fully through apertures (303, 315). When locking members (304) are in a fully closed position to provide a clear passageway through apertures (303, 315), the user can be reasonably certain that catheter (318) is properly coupled with injection port (312), such that a proper seal between catheter (318) and injection port (312) has been established, before suturing injection port (312) to tissue.

V. Exemplary Rotating Feature

Figure 12:
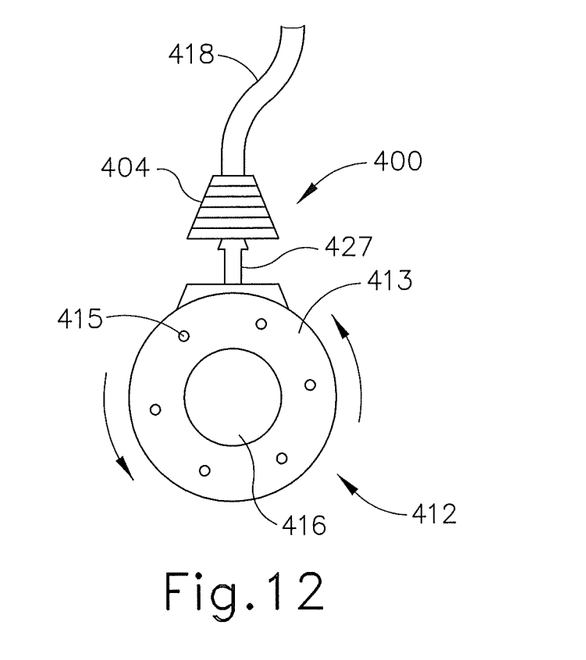
FIG. 12 depicts a top view of an exemplary injection port with a rotating disc in a closed position.
Figure 13:
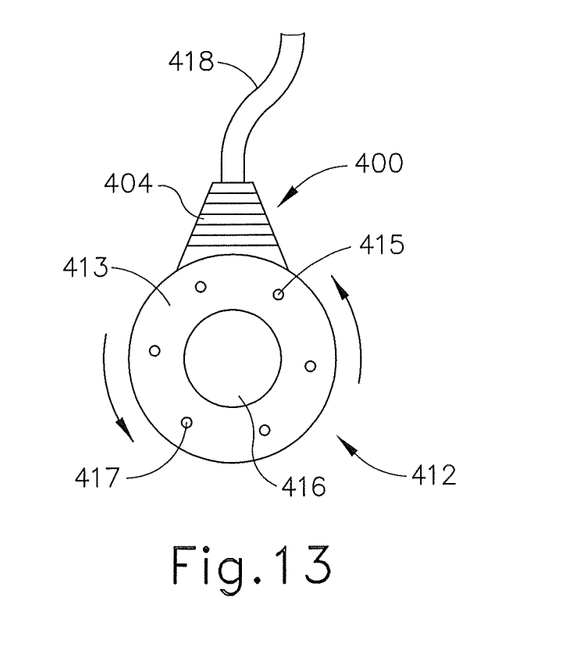
FIG. 13 depicts a top view of the injection port shown in FIG. 12 with the rotating disc in an open position.

FIGS. 12-13 show an exemplary injection port (412) having a rotating disc (413) mounted on top of injection port (412), though it should be understood that disc (413) may alternatively be mounted to the bottom of injection port (412). Injection port (412) also has a barbed stem (427) extending from injection port (412), to interface with catheter (418) like other barbed stems described herein. Injection port (412) is in selective communication with locking connector (400), which leads to catheter (418). Locking connector (400) comprises a locking member (404) that is operable to directly engage injection port (412) to secure catheter (418) to barbed stem (427) in order to establish fluid communication between catheter (418) and injection port (412).

Injection port (412) of the present example further comprises a septum (416) that is operable to receive a needle for providing fluid to catheter (418) via barbed stem (427). Disc (413) encircles septum (416) such that a needle may still be inserted into septum (416) even with disc (413) mounted on injection port (412). Disc (413) defines a plurality of disc openings (415), which form a circular pattern around the periphery of disc (413). However, any suitable arrangement for disc openings (415) may be used as would be apparent to one of ordinary skill in the art in view of the teachings herein. Disc openings (415) correspond to suture openings (417) that are formed in a lower annular flange of injection port (412). Disc (413) is rotatable between an open position and a closed position to selectively reveal suture openings (417) of injection port (412). When disc (413) is rotated to a closed position, as seen in FIG. 12, disc openings (415) do not align with suture openings (417) of injection port (412). Instead, disc (413) covers suture openings (417) while the lower flange of injection port (412) blocks the bottoms of disc openings (415) such that sutures cannot fully pass through either openings (415) or openings (417). As a result, sutures cannot pass through disc openings (415, 417) to secure injection port (412) to tissue when disc (412) is in the closed position. However, disc (413) may be rotated as shown in FIG. 13 to reveal suture openings (417). Thereafter, sutures may pass fully through aligned openings (415, 417) to secure injection port (412) to tissue in a patient.

In some versions, locking member (404) is operable to engage a switch, trigger, or other feature within injection port (412) to toggle disc (413) between the open and closed positions. For instance, disc (413) may be resiliently biased to the closed position (e.g., by a ribbon spring, etc.), and features of injection port (412) and/or locking member (404) may transition disc (413) to the open position, against the resilient bias, upon locking member (404) being fully seated against injection port (412). In some versions, simply engaging and securing the connection between locking member (404) and injection port (412) may be sufficient to switch disc (413) from open to closed and vice versa. In some other exemplary versions, engaging injection port (412) with locking member (404) may simply unlock disc (413) such that the user may manually turn disc (413) to either an open or closed state. It is also contemplated that injection port (412) may be configured such that disc (413) must be rotated in order to properly secure locking member (400) to injection port (412). In other words, if disc openings (415) and suture openings (417) are not aligned, then locking member (400) and injection port (412) cannot be properly secured. Other suitable ways of conditionally engaging locking member (400) with injection port (412) will be apparent to one of ordinary skill in the art in view of the teachings herein.

VI. Exemplary Injection Port with Hinge Feature

Figure 14:
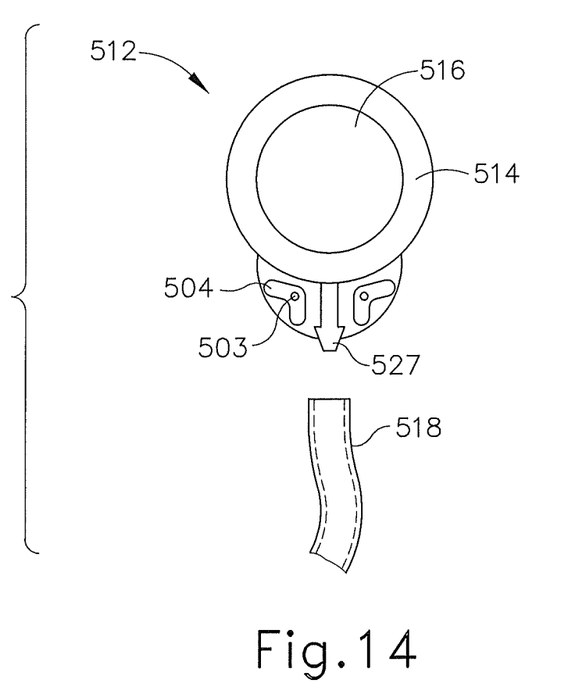
FIG. 14 depicts a top view of an exemplary injection port having a hinge feature in a closed position.
Figure 15:
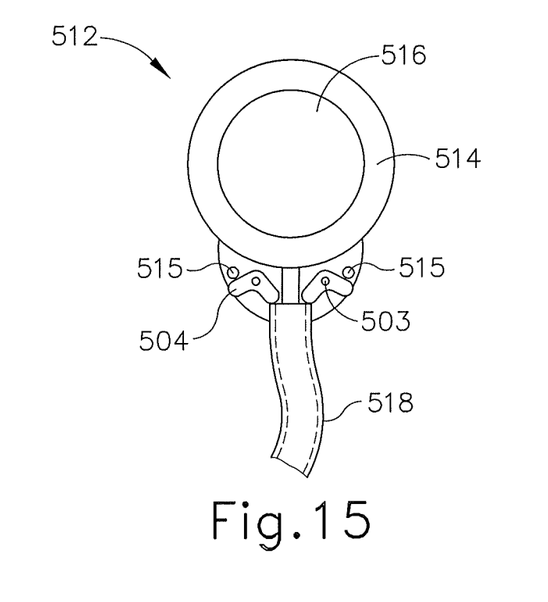
FIG. 15 depicts a top view of the injection port of FIG. 14 with the hinge feature in an open position.

FIGS. 14-15 show an exemplary injection port (512) having a pair of hinge features (504) pivotally mounted to a flange of housing (514) by respective pins (503). Injection port (512) also includes a septum (516) and a barbed stem (527), which is in fluid communication with a reservoir positioned under septum (516). Each hinge feature (504) is operable to transition between a closed position as shown in FIG. 14 and an open position as shown in FIG. 15. In the closed position, hinge features (504) cover respective suture apertures (515). As a result, suture thread cannot be guided through suture apertures (515) when hinge features (504) are in a closed position as shown in FIG. 14. When catheter (518) is pushed onto barbed stem (527) to establish fluid communication with injection port (512), hinge features (504) are engaged by catheter (518), which causes hinge features (504) to pivot about pins (503), thus moving hinge features (504) to the open position depicted in FIG. 15. Once hinge features (504) are moved to the open position, suture apertures (515) are revealed and sutures may be passed fully through suture apertures (515).

While the present example shows catheter (518) and hinge feature (504) interacting directly, in some other versions, the engagement with hinge feature (504) may be indirect through, for example, a retention sleeve, a flange, or any other suitable component as would be apparent to one of ordinary skill in the art in view of the teachings herein.

It should be understood that while the various examples described herein relate to the use of suture apertures and sutures to secure injection port (12) to a patient's tissue, the teachings herein may be readily applied to injection ports that are secured to a patient's tissue in various other ways. By way of example only, the teachings herein may be readily applied to injection ports that include integral fasteners, such as the injection ports disclosed in described in U.S. Pub. No. 2005/0283118, issued as U.S. Pat. No. 7,850,660, the disclosure of which is incorporated by reference herein. For instance, such injection ports may prevent the fasteners from being deployed until a catheter and/or retention sleeve, etc., is fully secured to the injection port. Various suitable ways in which the teachings herein may be combined with teachings of U.S. Pub. No. 2005/0283118, issued as U.S. Pat. No. 7,850,660, will be apparent to those of ordinary skill in the art in view of the teachings herein. Similarly, other suitable variations will be apparent to one of ordinary skill in the art in view of the teachings herein.

As mentioned previously, the injection ports described herein may be used as part of a gastric band system. By way of example, a gastric band is positioned in a patient in the manner described previously, and an injection port of the type described herein also implanted in the patient. One end of a fluid conduit is attached to the injection port, such as by mounting one end of the conduit over the injection port stem, and then fitting the retention sleeve attached to the housing over at least a portion of the conduit mounted to the stem such that the flexible fingers in the retention sleeve help prevent the conduit from being pulled off of the stem. The other end of the conduit is coupled to the gastric band in order to provide fluid communication between the gastric band and the reservoir of the injection port. The conduit may be coupled to the injection port and/or the gastric band either before or after those structures are implanted in the patient.

As yet another example, gastric band system (10) may include an implanted pump/reservoir system (not shown) instead of including an injection port (12). Such a pump/reservoir system may be controlled to selectively vary the amount of fluid in gastric band (20). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Such systems may include a catheter or other type of conduit coupling the pump/reservoir with gastric band (20). Accordingly, such systems may include any of the various suture opening alignment features described herein. Similarly, it should be understood that gastric band (20) may include any of the various suture opening alignment features described herein. Various suitable ways in which the suture opening alignment features described herein may be incorporated into a pump/reservoir and/or into a gastric band (20) will be apparent to those of ordinary skill in the art in view of the teachings herein.

It should be understood from the foregoing that conduit/catheter retention features such as those described herein may be incorporated into virtually any type of implanted device. The above described examples of gastric band systems are mere illustrations. The inventors' contemplation is not limited to components of gastric band systems. By way of example only, conduit/catheter retention features may be incorporated into an implanted drug infusion port, chemotherapy port, or any other type of implantable port that is used to deliver medication. Still other types of implanted devices that may incorporate conduit/catheter retention features will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implantable medical port comprising:
   (a) a port operable to fluidly communicate with an implantable band, wherein the port comprises a needle penetrable septum and a flange that extends from the port, wherein the port further comprises a pair of exterior apertures, and wherein the pair of exterior apertures extend through the flange;
   (b) a catheter in selective communication with the port, wherein the catheter is configured to establish fluid communication between the port and the implantable band, wherein the catheter is configured to deliver fluid from the port to the implantable band;
   (c) a stem in communication with the catheter, wherein the stem is configured to slidably receive the catheter and to secure the catheter relative to the port; and
   (d) a pair of L-shaped blocking members, wherein a first blocking member of the pair of blocking members is coupled to the flange on a first side of the stem and a second blocking member of the pair of blocking members is coupled to the flange on a second opposite side of the stem, wherein the first and second blocking members are each pivotally coupled to the flange with respective pins, wherein the blocking members are in spaced relation to the stem and are configured to selectively block a respective exterior aperture of the pair of exterior apertures when the catheter is decoupled from the stem and configured to selectively unblock a respective exterior aperture of the pair of exterior apertures in response to sliding the catheter about the stem, wherein the catheter is configured to bear against the blocking members and thereby pivot the blocking members relative to the port to unblock the pair of apertures as the catheter is coupled with the stem.

* * * * *